(12) United States Patent
Lee et al.

(10) Patent No.: US 11,826,730 B2
(45) Date of Patent: Nov. 28, 2023

(54) PRECURSOR OF CATALYST FOR HYDROGENATION OF CARBON DIOXIDE AND MANUFACTURING METHOD THEREFOR, AND HYDROGENATION CATALYST OF CARBON DIOXIDE AND MANUFACTURING METHOD THEREFOR

(71) Applicant: UNIST(ULSAN NATIONAL INSTITUTE OF SCIENCE AND TECHNOLOGY), Ulsan (KR)

(72) Inventors: Jae Sung Lee, Ulsan (KR); Yohan Choi, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 447 days.

(21) Appl. No.: 16/489,422

(22) PCT Filed: Feb. 28, 2017

(86) PCT No.: PCT/KR2017/002224
§ 371 (c)(1),
(2) Date: Aug. 28, 2019

(87) PCT Pub. No.: WO2018/159869
PCT Pub. Date: Sep. 7, 2018

(65) Prior Publication Data
US 2020/0009537 A1    Jan. 9, 2020

(51) Int. Cl.
*B01J 23/745* (2006.01)
*B01J 35/02* (2006.01)
(Continued)

(52) U.S. Cl.
CPC ......... *B01J 23/745* (2013.01); *B01J 35/026* (2013.01); *B01J 35/08* (2013.01); *B01J 35/10* (2013.01);
(Continued)

(58) Field of Classification Search
None
See application file for complete search history.

(56) References Cited

U.S. PATENT DOCUMENTS 4,618,597 A * 10/1986 Fiato ............... B01J 23/005
423/594.1
4,748,144 A * 5/1988 Monnier ........... B01J 23/002
502/316
(Continued)

FOREIGN PATENT DOCUMENTS

JP       2015-077575       4/2015
KR    10-2011-0008591       1/2011
(Continued)

OTHER PUBLICATIONS

Chonco et al ("Comparing silver and copper as promoters in Fe-based Fischer-Tropsch catalysts using delafossite as a model compound", J Cata 307 (2013) 283-294) (Year: 2013).*
(Continued)

*Primary Examiner* — Colin W. Slifka
*Assistant Examiner* — Michael Forrest
(74) *Attorney, Agent, or Firm* — LEX IP MEISTER, PLLC

(57) ABSTRACT

The present invention relates to a precursor of a hydrogenation catalyst of carbon dioxide, a method for preparing thereof, a hydrogenation catalyst of carbon dioxide, and a method for preparing thereof. An embodiment of the present invention provides a precursor of a hydrogenation catalyst of carbon dioxide comprising $CuFeO_2$.

8 Claims, 3 Drawing Sheets

CuFeO$_2$-1    CuFeO$_2$-2    CuFeO$_2$-3

(51) Int. Cl.
  B01J 35/08   (2006.01)
  B01J 35/10   (2006.01)
  B01J 37/04   (2006.01)
  B01J 37/10   (2006.01)
  B01J 37/16   (2006.01)
  C01G 49/00   (2006.01)
  C07C 1/12    (2006.01)

(52) U.S. Cl.
  CPC ........... *B01J 35/1014* (2013.01); *B01J 37/04* (2013.01); *B01J 37/10* (2013.01); *B01J 37/16* (2013.01); *C01G 49/0018* (2013.01); *C07C 1/12* (2013.01); *C01P 2002/72* (2013.01); *C01P 2002/76* (2013.01); *C01P 2002/78* (2013.01); *C01P 2004/03* (2013.01); *C01P 2004/04* (2013.01); *C01P 2004/32* (2013.01); *C01P 2004/62* (2013.01); *C01P 2006/12* (2013.01)

(56) References Cited

U.S. PATENT DOCUMENTS

2004/0009871 A1* 1/2004 Hu ..................... B01J 37/0036
                                                   502/338
2013/0274093 A1* 10/2013 Woodfield ........... B01J 35/1061
                                                   502/177

FOREIGN PATENT DOCUMENTS

KR   10-1790291    10/2017
WO   2012-052624   4/2012

OTHER PUBLICATIONS

Terada et al ("Correlation between crystal structure and magnetism in the frustrated antiferromagnet $CuFeO_2$ under high magnetic fields", Phys Rev B 75, 224411 (2007) pp. 224411-1 to 224411-8) (Year: 2007).*

Yo Han Choi et al., "Carbon dioxide Fischer-Tropsch synthesis: A new path to carbon-neutral fuels", Environmental, 2017, V.202, p. 605-610.

N. Utsis et al., "Novel bifunctional catalysts based on crystalline multi-oxide matrices containing iron ions for $CO_2$ hydrogenation to liquid fuels and chemicals", Faraday Discuss., 2016, 188, 545-563.

Dehua Xiong et al., "Hydrothermal synthesis of delafossite $CuFeO_2$ crystals at 100 degree C.", RSC Adv., 2015, 5, 49280-49286.

Youn Jeong Jang et al., "Oxygen-Intercalated $CuFeO_2$ Photocathode Fabricated by Hybrid Microwave Annealing for Efficient Solar Hydrogen Production", Chem. Mater. 2016, 28, 6054-6061.

Xiaoqing Qiu et al., "A facile one-step hydrothermal synthesis of rhombohedral $CuFeO_2$ crystals with antivirus property", Chem. Commun., 2012, 48, 7365-7367.

M. M. Moharam et al., "A facile novel synthesis of delafossite $CuFeO_2$ powders", Journal of Materials Science Materials in Electronics, 2014, 25; 1798-1803.

* cited by examiner

[FIG. 1]
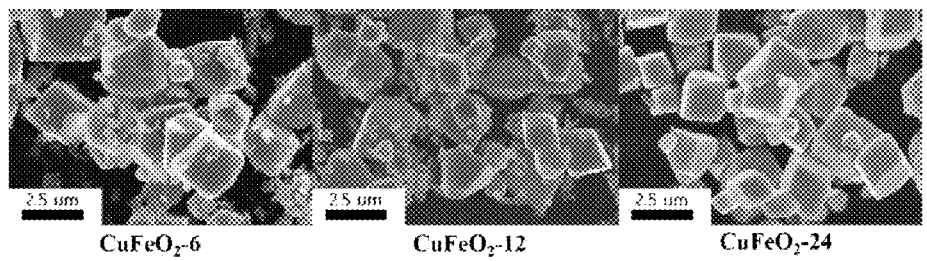
[FIG. 2]
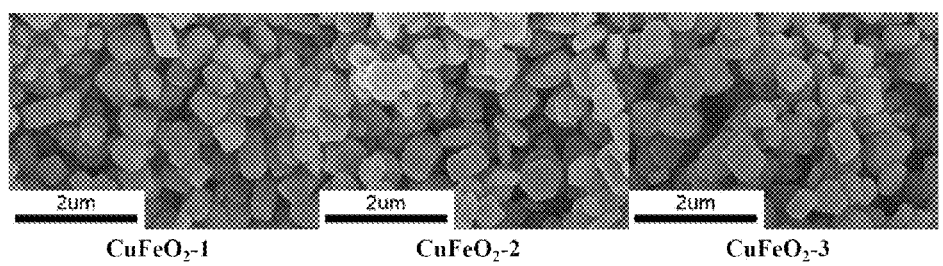
[FIG. 3]
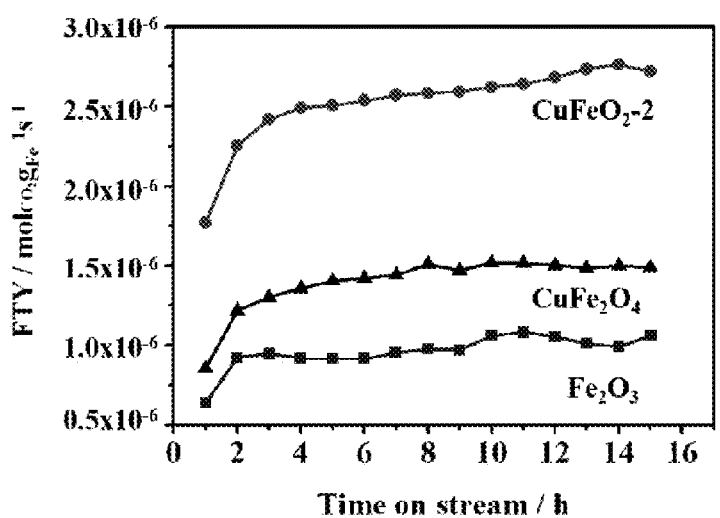

[FIG. 4]
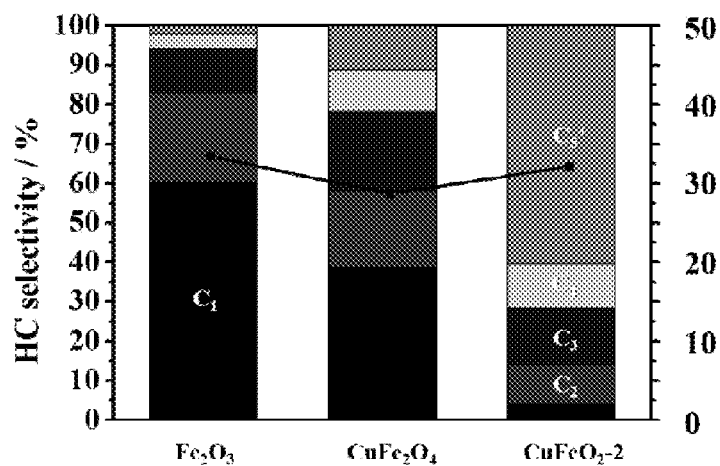
[FIG. 5]
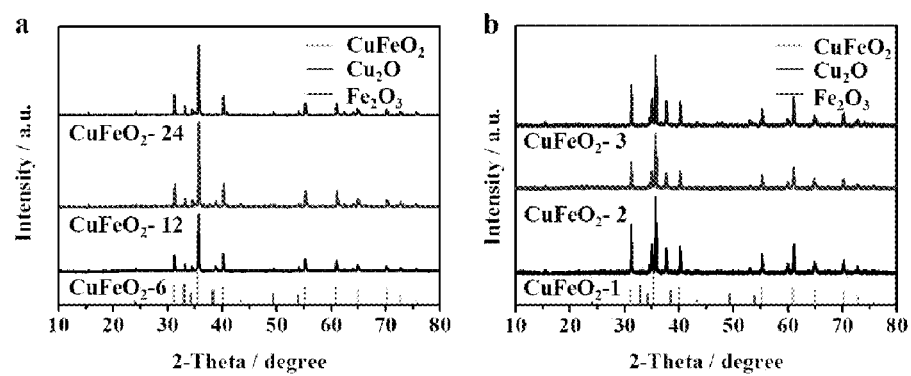

[FIG. 6]
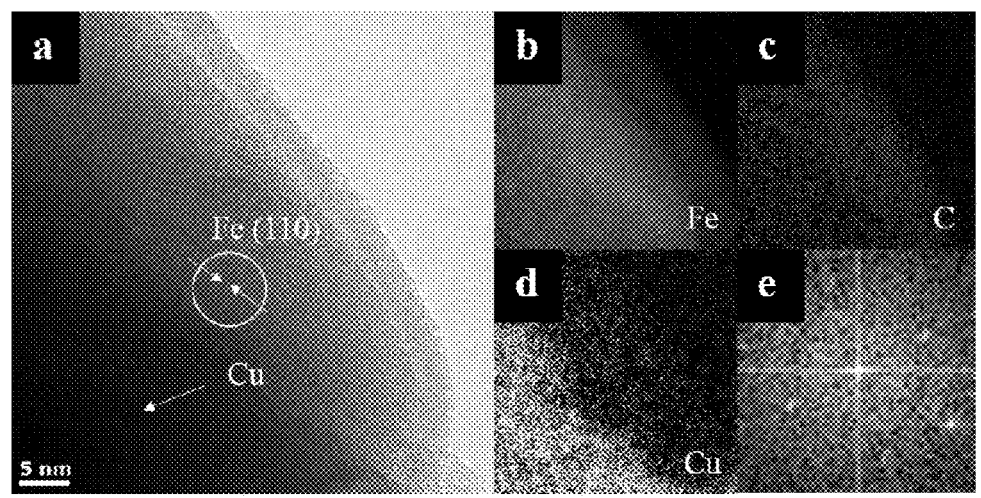

PRECURSOR OF CATALYST FOR HYDROGENATION OF CARBON DIOXIDE AND MANUFACTURING METHOD THEREFOR, AND HYDROGENATION CATALYST OF CARBON DIOXIDE AND MANUFACTURING METHOD THEREFOR

Precursor of the hydrogenation catalyst of carbon dioxide, and method for manufacturing thereof, hydrogenation catalyst of carbon dioxide, and method for manufacturing thereof.

FIELD OF THE INVENTION

The present invention relates to a precursor of a hydrogenation catalyst of carbon dioxide, and method for manufacturing thereof, a hydrogenation catalyst of carbon dioxide, and method for manufacturing thereof.

TECHNICAL BACKGROUND OF THE INVENTION

Recently, research has been actively conducted to convert carbon dioxide gas, one of the main causes of climate change, into chemical fuels or high value materials.

Accordingly, investment in a catalyst for carbon dioxide hydrogenation is also actively made.

However, the material produced by the catalyst in the carbon dioxide hydrogenation is limited to a hydrocarbon gas having a low molecular weight.

More specifically, there are difficulties in producing hydrocarbon gases with high molecular weight such as liquid fuels or higher value olefins suitable for transport.

Thus, in an embodiment of the present invention will be describe later for a catalyst, a precursor of the catalyst and a method for manufacturing the same that may produce materials such as liquid hydrocarbons and olefins from carbon dioxide hydrogenation.

CONTENTS OF THE INVENTION

Problem to Solve

An embodiment of the present invention provides a precursor of the hydrogenation catalyst of carbon dioxide, a method for manufacturing thereof, a hydrogenation catalyst of carbon dioxide, and a method for manufacturing thereof.

SUMMARY OF THE INVENTION

A precursor of the hydrogenation catalyst of carbon dioxide according to an embodiment of the present invention may comprise $CuFeO_2$ having a particle diameter is 800 nm or less.

The precursor may comprise a trigonal form.

A method for manufacturing a precursor of the hydrogenation catalyst of carbon dioxide according to another embodiment of the present invention may comprise, preparing an iron raw material and a copper raw material; adding the iron and copper raw materials into a solvent to prepare a solution; adding a reduction agent into the solution; and hydrothermal-synthesizing the solution in which the reduction agent is added to prepare a catalyst precursor.

At this time, the iron raw material is $FeCl_2$.

the solution may be hydrothermally synthesized in the temperature range of 150 to 200° C. by the step of hydrothermal-synthesizing the solution in which the reduction agent is added to prepare a catalyst precursor.

The solution may be hydrothermal-synthesized for 30 minutes to 5 hours

The copper raw material may be $Cu(NO_3)_2$, CuCl or a combination thereof in the step of preparing an iron raw material and a copper raw material.

The raw materials may be added to 5 to 10 parts by weight with respect to 100 parts by weight of the solvent in the step of adding the raw materials into a solvent to prepare a solution.

More specifically, sodium hydroxide (NaOH) may be further added.

Even more specifically, Sodium hydroxide may be further added to 6 to 11 parts by weight with respect to 100 parts by weight of the solution.

The reduction agent may comprise propionaldehyde, Ethylene glycol or a combination thereof in the step of adding a reduction agent into the solution.

More specifically, the reduction agent may be added to more than 0 and 3 parts by weight or less with respect to 100 parts by weight of the solution.

A hydrogenation catalyst of carbon dioxide according to another embodiment of the present invention may be comprised Cu and Fe; and a trigonal form.

A specific surface area of the catalyst may be 10 m²/g or more.

A particle diameter of the catalyst may be 800 nm or less.

More specifically, it may be 500 to 800 nm.

The porosity of the catalyst may be 0.12 to 0.17 cm³/g.

A weight ratio of Cu-to-Fe (Cu/Fe) of the catalyst may be 0.594 or more.

A distance of the Fe metal (110) lattice plane of the catalyst may be 0.2 nm or more.

Spherical Cu particles may be located on the surface of the catalyst.

Fe time yield (FTY—mol of $CO_2$ converted per g of Fe in the catalyst per second) may be $1.7 \times 10^{-6}$ $molco_2 g_{fe}^{-1} s^{-1}$ or more.

An olefin-to-paraffin (O/P) ratio of the catalyst may be 9.0 or more.

The catalyst is used for the hydrogenation reaction of carbon dioxide, the product of the reaction comprises hydrocarbon, the hydrocarbon having the carbon number of C5 or more may be 59 wt % or more, with respect to 100 wt % of hydrocarbons in the product.

The hydrocarbon having the carbon number of C1 may be 6 wt % or less, with respect to 100 wt % of hydrocarbons in the product.

A method for preparing a hydrogenation catalyst of carbon dioxide according to anther embodiment of the present invention may comprise preparing an iron raw material and a copper raw material; adding the raw materials into a solvent to prepare a solution; adding a reduction agent into the solution; hydrothermal-synthesizing the solution in which the reduction agent is added to prepare a catalyst precursor; and reducing the prepared catalyst precursor.

At this time, the iron raw material is $FeCl_2$.

The catalyst precursor may be reduced in the temperature range of 200 to 500° C. in the step of reducing the prepared catalyst precursor.

The catalyst precursor may be reduced for 1 to 5 hours

More specifically, the catalyst precursor is reduced under a hydrogen gas atmosphere, and the flow rate of the hydrogen gas may be 50 to 200 sccm.

The catalyst obtained by the step of reducing the prepared catalyst precursor comprises Cu and Fe; and a trigonal form, and may provide a catalyst which a specific surface area is 10 m²/g or more.

The catalyst precursor prepared by the step of hydrothermal-synthesizing the solution in which the reduction agent is added may comprise $CuFeO_2$ having a particle diameter is 800 nm or less.

The prepared catalyst precursor may be in trigonal form.

Effect of the Invention

According to an embodiment of the present invention, the catalyst may be easily prepared at a low temperature using a delafossite precursor.

Further, the prepared catalyst may be used for carbon dioxide hydrogenation.

In addition, the catalyst may excellently improve the production of hydrocarbon with high molecular weight.

BRIEF DESCRIPTION OF THE DRAWINGS

FIG. 1 is a SEM observation of the precursor of catalyst according to comparative examples 2 to 4.

FIG. 2 is a SEM observation of the precursor of the catalyst according to embodiment 1 to 3.

FIG. 3 is a graph disclosing the yield of Fe metal according to time in embodiment 2, comparative example 1, and comparative example 5.

FIG. 4 is a graph showing hydrocarbon selectivity of embodiment 2, comparative example 1, and comparative example 5.

FIG. 5 shows the analysis results of XRD of the catalysts according to comparative examples 1 to 3 and embodiment 1 to 3.

FIG. 6 is a TEM photograph showing the Fe lattice plane.

DETAILED DESCRIPTION OF THE EMBODIMENT

Advantages and features of the present invention; and methods of achieving the same; will become apparent with reference to the embodiments described below in detail in conjunction with the accompanying drawings.

However, the present invention is not limited to the embodiments disclosed below, but may be embodied in several different forms, and the present embodiments merely provided to complete the disclosure of the present invention and to be fully inform the scope of the present invention to those who is having ordinary knowledge of the technical field to which the present invention belongs and the invention is defined by the scope of the claims.

Same reference numerals refer to same elements throughout the specification.

Therefore, in some embodiments, well known techniques are not described in detail in order to avoid interpreting obscurely the present invention.

Although not defined differently, every term (comprising technical and scientific terms) used herein have the same meaning as commonly understood by those who is having ordinary knowledge of the technical field to which the present invention belongs.

When any part of the specification "comprise" any elements, this means that it may further comprise other elements, except to exclude other elements unless otherwise stated.

Further, singular forms also comprise the plural forms unless otherwise stated specifically.

According to an embodiment of the present invention may provide a precursor of the hydrogenation catalyst of carbon dioxide, comprising $CuFeO_2$ having a particle diameter of 800 nm or less.

More specifically, it may comprise CuFeO2 having particle diameter of 500 to 800 nm.

By using the catalyst precursor having a small particle diameter, the hydrothermal-synthesizing time may be reduced in the step of preparing a catalyst precursor described later.

Further, the particle diameter of the prepared hydrogenation catalyst thereby may also be as small as the above range.

For this reason, an olefin-to-paraffin (O/P) ratio may be high.

Therefore, the selectivity of the liquid hydrocarbon may be improved.

Hereinafter, a particle diameter in this specification means the average diameter of the spherical material which presents in a measuring unit.

If the material is non-spherical, it means the diameter of the sphere calculated by approximating the non-spherical material to the sphere.

The precursor may be a delafossite.

Further, the precursor may be in trigonal form.

However, the present invention is not limited thereto.

A method for manufacturing a precursor of the hydrogenation catalyst of carbon dioxide according to another embodiment of the present invention may comprise, preparing an iron raw material and a copper raw material; adding the raw materials into a solvent to prepare a solution; adding a reduction agent into the solution; and hydrothermal-synthesizing the solution in which the reduction agent is added to prepare a catalyst precursor.

First, the step of preparing an iron raw material and a copper raw material; may be performed.

The iron raw material may be $FeCl_2$

Further, the copper raw material may be $Cu(NO_3)_2$, CuCl, or a combination thereof, but is not limited thereto.

Thereafter, the step of adding the raw material into a solvent to prepare a solution; may be performed.

The raw materials may be added to 5 to 10 parts by weight with respect to 100 parts by weight of the solvent.

More specifically, it may be added in 6 to 9 parts by weight, or 7 to 9 parts by weight.

More specifically, it may be added to 8 to 9 parts by weight or 8.03 to 8.06 parts by weight.

When the amount is satisfied, the amount of impurities may be reduced.

At this time, the impurities may be $Fe_2O_3$, $Cu_2O$ or a combination thereof.

Further, 0.05 to 0.1 mol of sodium hydroxide (NaOH) may be further added to the solution.

For 100 parts by weight of the solution, the sodium hydroxide may be further added to 6 to 11 parts by weight.

More specifically, with respect to 100 parts by weight of the solution, the sodium hydroxide may be further added to 8 to 11 parts by weight.

Even more specifically, with respect to 100 parts by weight of the solution, the sodium hydroxide may be further added to 9 to 11 parts by weight.

This is to control the basicity of the solution in the range of pH 11 to 13, it may have a rhomboheral structure by controlling the basicity of the solution.

Thereafter, the step of adding a reduction agent into the solution; may be performed.

More specifically, the reduction agent may comprise propionaldehyde, Ethylene glycol or a combination thereof.

However, it is not limited thereto.

For 100 parts by weight of the solution, the reduction agent may be added to more than 0 and 3 parts by weight or less.

More specifically, with respect to 100 parts by weight of the solution, the reduction agent may be added to 1 to 3 parts by weight.

Even more specifically, with respect to 100 parts by weight of the solution, the reduction agent may be added to 2 to 3 parts by weight.

Even more specifically, the reason for adding such a reduction agent is to derive the effect that copper ions are reduced to monovalent.

Finally, the step of hydrothermal-synthesizing the solution in which the reduction agent is added to prepare a catalyst precursor may be performed.

At this time, the solution may be hydrothermal-synthesized in a temperature range of 150 to 200° C.

Further, the solution may be hydrothermal-synthesized for 30 minutes to 5 hours.

More specifically, delafossite may be synthesized at low temperature by hydrothermal-synthesizing the solution for the above temperature and time.

Even more specifically, it may be hydrothermal-synthesizing using microwaves.

However, it is not limited thereto.

The hydrogenation catalyst of carbon dioxide according to another embodiment of the present invention, comprises Cu and Fe, comprising a trigonal form, may provide a hydrogenation catalyst of carbon dioxide that has a specific surface area of 10 m$^2$/g or more.

More specifically, a specific surface area of the catalyst may be 10 m$^2$/g or more.

More specifically, it may be 10 to 15 m$^2$/g.

More specifically, if the specific surface area of the catalyst is within the above range, micropores may occur after the hydrogenation processing.

Specific surface area may be measured by $N_2$ adsorption-and-desorption method.

More specifically, the catalyst comprising Cu and Fe may be derived the trigonal precursor described above.

Therefore, the catalyst may comprise a trigonal form as the precursor described above.

Further, since the catalyst is in a reduced form of the precursor described above, the catalyst may have more surface porosity than the precursor described above.

The porosity of the catalyst may be 0.1 to 0.2 cm$^3$/g.

More specifically, the porosity of the catalyst may be 0.1 to 0.18 cm$^3$/g.

Even more specifically, it may be 0.12 to 0.17 cm$^3$/g.

Even more specifically, if the specific surface area and porosity of the catalyst prepared by reduction are within the above ranges, the reaction rate may be improved. Further, there may be an effect that the liquid hydrocarbon is easily desorbed.

Further, the weight of Cu-to-Fe (Cu/Fe) of the catalyst may be 0.59 or more.

More specifically, the weight of Cu-to-Fe (Cu/Fe) of the catalyst may be 0.594 or more.

Even more specifically, the weight of Cu-to-Fe (Cu/Fe) of the catalyst may be 0.591 to 0.595.

Even more specifically, it may be 0.594 to 0.5941.

If the weight of Cu element-to-Fe element (Cu/Fe) of the catalyst is within the above range, a trigonal CuFeO2 may be synthesized with high purity.

Further, the spherical Cu particles may be located on the surface of the catalyst.

More specifically, some or all of the entire Cu particles may be located as spherical on the surface of the catalyst.

The ratio of Cu particles present on the catalyst surface may be 50 to 80 wt % in 100 wt % of the total Cu particles.

As described above, if Cu is on the surface of the catalyst, Fe may be easily and completely reduced.

The distance of the Fe metal (110) lattice plane of the catalyst may be 0.2 nm or more.

More specifically, the distance of the Fe metal (110) lattice plane of the catalyst may be 0.2 nm to 0.21 nm.

More specifically, it may be 0.2 to 0.201 nm.

This may be confirmed in FIG. 6.

If the distance of the Fe metal (110) lattice plane of a catalyst is within the above range, a large amount of Fe carbide which is an active site is synthesized, thereby may have the high selectivity of the liquid hydrocarbon.

The FTY (Fe time yield) value of the catalyst may be greater than or equal to $1.7 \times 10^{-6}$ $molco_{2}g_{fe}^{-1}s^{-1}$.

O/P (olefin-to-paraffin ratio) value of the catalyst may be 9.0 or more.

More specifically, it may be 9.5 or more.

More specifically, the FTY (Fe time yield) value of the catalyst means a change amount of carbon dioxide per unit iron, and per unit time.

Further, the O/P (olefin-to-paraffin) value of the catalyst means the olefin-to-paraffin (O/P) ratio of the catalyst.

Even more specifically, if the FTY value and the O/P value has the above range, there may be an effect of increasing the selectivity of the liquid hydrocarbon.

The catalyst may be used for the hydrogenation of carbon dioxide, and the product by the reaction may comprise a hydrocarbon.

More specifically, with respect to 100 wt % of hydrocarbons in the product, hydrocarbons having the carbon number of C5 or more may be 59 wt % or more.

More specifically, it may be 60 wt % or more.

Even more specifically, it may be 63 wt % or more.

The higher the conversion ratio is the better, but may theoretically be 100 wt % or 99 wt % or less.

Further, with respect to 100 wt % of hydrocarbons in the product, hydrocarbons having the carbon number of C1 may be 6 wt % or less.

More specifically, it may be 5.6 wt % or less.

Finally, a method for preparing the carbon dioxide hydrogenation catalyst according to anther embodiment of the present invention may comprise preparing an iron raw material and a copper raw material; adding the raw materials into a solvent to prepare a solution; adding a reduction agent into the solution; hydrothermal-synthesizing the solution in which the reduction agent is added to prepare a catalyst precursor; and reducing the prepared catalyst precursor.

First, the step of preparing the iron raw material and a copper raw material; adding the raw materials into a solvent to prepare a solution; adding a reduction agent into the solution; and hydrothermal-synthesizing the solution in which the reduction agent is added to prepare a catalyst precursor are same as the method for manufacturing a precursor of the catalyst described above, detailed description thereof will be omitted below.

Thereafter, reducing the prepared catalyst precursor; may be further performed.

The catalyst precursor may be reduced in the temperature range of 200 to 500° C.

More specifically, it may be reduced at 300 to 500° C.

The catalyst precursor may be reduced for 1 to 5 hours.

More specifically, it may be reduced for 1 to 4 hours.

Even more specifically, it may be reduced for 1 to 3 hours.

More specifically, the catalyst precursor may be completely converted to Fe metal which is an active point, by reducing during the temperature range and the time.

Further, the catalyst precursor may be reduced under a hydrogen gas atmosphere in the step of reducing the prepared catalyst precursor.

At this time, the flow rate of the hydrogen gas may be 50 to 200 sccm.

More specifically, the flow rate of the hydrogen gas may be 50 to 150 sccm.

By limiting the flow rate of the hydrogen gas as described above, the delafossite may be completely reduced to the Fe metal.

More specifically, the carbon dioxide hydrogenation catalyst may be obtained by the step of reducing the prepared catalyst precursor.

The obtained catalyst comprises Cu and Fe, is in a trigonal form, and may have a specific surface area of 10 $m^2/g$ or more.

Even more specifically, it may be 15 $m^2/g$ or more.

Embodiment and Comparative Example

Catalyst reparation Method: Embodiment

A solution was prepared by dissolving 0.99 g of $FeCl_2.4H_2O$ and 1.2 g of $Cu(NO_3)_2.3H_2O$ in 40 ml of distilled water.

Thereafter, 4 g of NaOH of 0.1 mol was added to the solution and then stirred for 10 to 30 minutes.

Further, 0.5 ml of propionaldehyde was added to the solution to prepare a mixture.

The mixture was transferred to 100 ml of Teflon tube and then carried out hydrothermal at 180 180° C. for 1 to 3 hours.

This is equivalent to doing hydrothermal reaction for 12 to 36 hours in a Teflon-lined stainless steel autoclave.

As a result, $CuFeO_2$-1, $CuFeO_2$-2 and $CuFeO_2$-3 catalysts synthesized by hydrothermal for 1 hour, 2 hours, and 3 hours were prepared.

Catalyst reparation Method: Comparative Example

A solution was prepared by dissolving 2.02 g of $Fe(NO_3)_3.9H_2O$ and 1.2 g of $Cu(NO_3)_2.3H_2O$ in 40 ml of distilled water.

Thereafter, 4 g of NaOH of 0.1 mol was added to the solution, followed by stirring for 30 minutes.

Further, 0.5 ml of propionaldehyde was added to the solution to prepare a mixture.

The mixture was transferred to a 100 ml of Teflon-lined stainless steel autoclave and then carried out hydrothermal at 180° C. for 6 to 24 hours.

As a result, $CuFeO_2$-6, $CuFeO_2$-12 and $CuFeO_2$-24 catalysts synthesized by hydrothermal for 6 hours, 12 hours, and 24 hours were prepared as comparative examples 2 to 4, respectively.

Further, a $CuFe_2O_4$ catalyst which is a spinel structured nanopowder (less than 100 nm) was purchased from Sigma-Aldrich and prepared as comparative example 1.

Further, pure $Fe_2O_3$ was purchased from Kanto and prepared as comparative example 5.

Further, the mixture which mixed $Cu_2O$—$Fe_2O_3$ in the weight ratio of 1:1 respectively was prepared as comparative example 6.

Carbon Dioxide Hydrogenation Using Catalyst

The carbon dioxide hydrogenation by the catalyst was carried out in a fixed bed of a stainless steel reactor which is $CO_2/H_2$=1:3.

First, pre-reduction was carried out under of 100 sccm atmosphere of pure $H_2$ gas at 400° C. for 2 hours.

For catalytic reaction, $CO_2$ and $H_2$ gas were supplied into the reactor along with nitrogen gas.

At this time, the reducing conditions were 300° C., 10 bar and gas space velocity per hour were 1800 $mlg^{-1}h^{-1}$.

Further, the concentrations of $CO_2$, CO product and nitrogen were measured by an on-lined Agilent 7890A gas chromatograph with a thermal conductivity detector and a Carboxen 1000 packed column.

Hydrocarbon of $C_1$-$C_6$ were analyzed by GC such as a flame ionization detector and an Alumina Sulfate LOT Capillary column.

As a result, hydrocarbon products with high molecular weight were collected in a cold trap.

Further, the composition of the hydrocarbon with high molecular weight was calculated by wt % of carbon number using simulated distillation (SIMDIS) analysis.

Experimental Example

TABLE 1

| Catalyst | | Carbon dioxide conversion ratio, % | Carbon Monoxide Selectivity, % | Hydrocarbon selectivity (Excluding Monoxide), % | | | | | O/P |
|---|---|---|---|---|---|---|---|---|---|
| | | | | C1 | C2 | C3 | C4 | C5+ | |
| Embodiment 1 | $CuFeO_2$-1 | 17.5 | 33.8 | <u>5.6</u> | 10.0 | 14.1 | 11.0 | <u>59.3</u> | <u>10.3</u> |
| Embodiment 2 | $CuFeO_2$-2 | 20.2 | 25.8 | <u>4.8</u> | 8.8 | 13 | 10.3 | <u>63.1</u> | <u>9.9</u> |
| Embodiment 3 | $CuFeO_2$-3 | 18.9 | 30.7 | <u>5.2</u> | 9.6 | 13.9 | 11.0 | <u>60.3</u> | <u>9.7</u> |
| Comparative Example 1 | $Fe_2O_3$ | 14.3 | 33.2 | 60.2 | 22.5 | 11.3 | 3.7 | 2.3 | 0.03 |
| Comparative Example 2 | $CuFeO_2$-6 | 17.3 | 31.7 | <u>2.7</u> | 8.3 | 12.6 | 10.1 | <u>66.3</u> | 7.3 |
| Comparative Example 3 | $CuFeO_2$-12 | 18.1 | 31.9 | <u>3.9</u> | 10 | 14.5 | 11.3 | <u>60.3</u> | 7 |
| Comparative Example 4 | $CuFeO_2$-24 | 16.7 | 31.4 | <u>2.4</u> | 8.7 | 13.3 | 10.7 | <u>64.9</u> | 7.7 |
| Comparative Example 5 | $CuFe_2O_4$ | 13.3 | 28.4 | 38.3 | 19.7 | 20.1 | 10.5 | 11.4 | 0.02 |
| Comparative Example 6 | $Cu_2O$—$Fe_2O_3$ | 15.7 | 28.9 | 57.6 | 22.8 | 12.6 | 4.4 | 2.6 | 0.03 |

TABLE 2

| Catalyst | | Specific surface area, m²/g | Particle diameter | Present crystal system | Porosity | Weight ratio (Cu/Fe) |
|---|---|---|---|---|---|---|
| Embodiment 1 | CuFeO$_2$-1 | Unevaluated | 800 nm or less | Rhomboheral, hexagonal | Unevaluated | 1.13 |
| Embodiment 2 | CuFeO$_2$-2 | 10.2 | 800 nm or less | Rhomboheral, hexagonal | 0.166 | 1.13 |
| Embodiment 3 | CuFeO$_2$-3 | Unevaluated | 800 nm or less | Rhomboheral, hexagonal | Unevaluated | 1.13 |
| Comparative Example 1 | Fe$_2$O$_3$ | 12.4 | Unevaluated | Unevaluated | 0.143 | 0 |
| Comparative Example 2 | CuFeO$_2$-6 | Unevaluated | 2.5 μm level | rhomboheral | Unevaluated | 0.593 |
| Comparative Example 3 | CuFeO$_2$-12 | 10.3 | 2.5 μm level | rhomboheral | 0.12 | 0.593 |
| Comparative Example 4 | CuFeO$_2$-24 | Unevaluated | 2.5 μm level | rhomboheral | Unevaluated | 0.593 |
| Comparative Example 5 | CuFeO$_2$O$_4$ | 28.1 | Unrated | spherical | 0.403 | Unevaluated |

\* Unevaluated data for which no evaluation results were derived at the time of application.

As shown in Table 1, the embodiment of the present invention, compared to the comparative example, it may be seen that the carbon dioxide conversion ratio, the selectivity of the hydrocarbon having a carbon number of C5 or more, and O/P values are all superior.

More specifically, embodiments 1 to 3 of the present invention differ only in the iron precursor, compared to the comparative examples 2 to 4, and the catalyst was prepared under the same conditions.

As a result, embodiments 1 to 3, compared with comparative examples 2 to 4, the O/P value was significantly superior, and reduced hydrothermal-synthesizing time may be confirmed This result is derived from the fact that the iron precursors of embodiment 1 to 3 of the present invention are different from the iron precursors of comparative examples 2 to 4.

More specifically, this is because the particle diameter of the catalyst by the embodiment of the present invention is smaller than the particle diameter of the catalyst by the comparative example.

This may also be confirmed through FIGS. 1 and 2 of the present invention.

FIG. 1 is a SEM observation of the precursor of catalyst according to comparative examples 2 to 4.

FIG. 2 is a SEM observation of the precursor of the catalyst according to embodiment 1 to 3.

As shown in FIG. 2, the embodiment of the present invention may confirm that the particle diameter of the catalyst precursor is level 500 to 800 nm.

However, as shown in FIG. 1, it may be seen that the particle diameter of the catalyst precursor of the comparative example is 1 to 2.5 μm level.

Like this, the embodiment of the present invention, compared to comparative example, may improve the selectivity (O/P) of the liquid hydrocarbon by using a catalyst precursor having a smaller particle diameter.

Moreover, the catalyst could be prepared through hydrothermal-synthesizing in a short time.

Further, through FIG. 3 of the present invention, the embodiment of the present invention, compared to the comparative example, the superior characteristics of a change amount of carbon dioxide may be seen.

FIG. 3 is a graph disclosing the yield of Fe metal according to time in embodiment 2, comparative example 1, and comparative example 5.

More specifically, FIG. 3 is a graph showing a FTY (Fe time yield) value of the catalyst according to time, and the FTY (Fe time yield) value of the catalyst means that a change amount of carbon dioxide per unit iron, per unit time.

Accordingly, it may be seen that the FTY value of the example is $1.7 \times 10^{-6}$ molco$_2$g$_{fe}^{-1}$s$^{-1}$ or more, and it may be seen that a change amount of carbon dioxide of comparative example 1 and comparative example 5 is lower than that of the example.

Through FIG. 4 of the present invention, hydrocarbon selectivity according to carbon number may be confirmed using the catalysts by embodiments and comparative examples.

FIG. 4 is a graph showing hydrocarbon selectivity of embodiment 2, comparative example 1, and comparative example 5.

As disclosed in FIG. 4, embodiment 1 and 5, compared to comparative examples 1 and 5, it may be seen that the selectivity of carbon number with a large molecular weight of C5 or more is significantly higher.

This, as shown in Table 1, the embodiment of the present invention confirmed that the ratio of the olefin-to-paraffin is 9.0 or more, corresponding to the high effect of increasing the selectivity of the liquid hydrocarbon.

FIG. 5 shows the analysis results of XRD of the catalysts according to comparative examples 1 to 3 and embodiment 1 to 3.

More specifically, in the case of comparative examples 1 to 3, presenting the delafossite CuFeO$_2$ of the rhombohedral shape and the impurities Fe$_2$O$_3$ and CuO may be confirmed through the XRD peak.

However, in the case of Embodiments 1 to 3, it may be seen that only CuFeO$_2$ mixed with a rhombohedral shape and a hexagonal shape is present.

(Trigonal and hexagonal may be classified into the same classification. More specifically, the trigonal is a crystal system with three axes of symmetry and is also treated as a hexagonal.)

From this, the embodiment of the present invention compared to the comparative example, may improve the selectivity of liquefied hydrocarbons and the ratio of olefins and paraffins by preparing CuFeO$_2$ which is purer.

That is, the catalyst by the present invention has been confirmed that carbon dioxide may be easily converted into high value materials such as diesel and gasoline due to the high selectivity of the hydrocarbon with high molecular weight.

FIG. 6 is an HR-TEM and EELS mapping photograph of the Fe lattice plane of example 2.

From the FIG. 6, it may be confirmed that the active point is created during the iron carbide in reaction since C is present in Fe.

Further, as a result of confirming the lattice plane in the TEM photograph, it may be seen that the surface is 110 nm about 0.2 nm.

Although the embodiments of the present invention were described with reference to the accompanying drawings, those who is having ordinary knowledge of the technical field to which the present invention belongs may understand that it may be carried out in detailed forms without departing from the technical ideas or essential features of the present invention.

Therefore, the above-mentioned embodiments should be understood to be illustrative in all aspects and not limited thereto.

The scope of the present invention is shown by the claims described below rather than the detailed description, and all modifies or modified forms derived from the meaning and scope of the claims and their equivalent notion should be understood as being comprised in the scope of the present invention.

What is claimed is:

1. A hydrogenation catalyst of carbon dioxide comprising:
   Cu and Fe; and
   a trigonal form;
   wherein a specific surface area is 10 to 15 $m^2/g$,
   wherein the catalyst is used for a hydrogenation reaction of carbon dioxide,
   wherein a product of the reaction comprises olefins and paraffins,
   wherein an olefin-to-paraffin (O/P) ratio of the catalyst is 9.0 or more, and
   wherein a particle diameter of the catalyst is 500 to 800 nm.

2. The hydrogenation catalyst of carbon dioxide of claim 1, wherein the porosity of the catalyst is 0.12 to 0.17 $cm^3/g$.

3. The hydrogenation catalyst of carbon dioxide of claim 2, wherein a weight ratio of Cu-to-Fe (Cu/Fe) of the catalyst is 0.594 or more.

4. The hydrogenation catalyst of carbon dioxide of claim 3, wherein a distance of the Fe metal (110) lattice plane of the catalyst is 0.2 nm or more.

5. The hydrogenation catalyst of carbon dioxide of claim 4, wherein spherical Cu particles are located on the surface of the catalyst.

6. The hydrogenation catalyst of carbon dioxide of claim 5, wherein Fe time yield (FTY—mol of $CO_2$ converted per g of Fe in the catalyst per second) is $1.7 \times 10^{-6}$ $molco_2 g_{fe}^{-1} s^{-1}$ or more.

7. The hydrogenation catalyst of carbon dioxide of claim 5,
   wherein the catalyst is used for the hydrogenation reaction of carbon dioxide,
   wherein the product of the reaction comprises hydrocarbon,
   wherein a hydrocarbon having a carbon number of C5 or more is 59 wt % or more, with respect to 100 wt % of hydrocarbons in the product.

8. The hydrogenation catalyst of carbon dioxide of claim 7, wherein a hydrocarbon having a carbon number of C1 is 6 wt % or less, with respect to 100 wt % of hydrocarbons in the product.

* * * * *